US00PP13134P2

(12) United States Plant Patent
Zaiger et al.

(10) Patent No.: US PP13,134 P2
(45) Date of Patent: Oct. 29, 2002

(54) INTERSPECIFIC TREE NAMED 'BLACK KAT'

(76) Inventors: Chris Floyd Zaiger, 929 Grimes Ave., Modesto, CA (US) 95358; Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 87 days.

(21) Appl. No.: 09/832,152

(22) Filed: Apr. 10, 2001

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct variety of interspecific tree [plum×(plum×plumcot)]; the features of the tree and its fruit are characterized by the tree budded on 'Nemaguard' Rootstock (non-patented), grown on Handford sandy loam soil with Storie Index rating 95, in USDA Hardiness zone 9, near Modesto, Calif., and with standard commercial cultural fruit practices such as pruning, thinning, spraying, irrigation and fertilization. Its novelty consists of the following unique combination of features that are desirable in a new variety:

1. Heavy and regular production of large fruit.
2. Fruit with an attractive blue-black skin color.
3. Fruit with very good flavor and eating quality.
4. Fruit with high soluble solids, averaging 19.9° Brix.
5. Fruit with firm flesh, good handling and shipping quality.

1 Drawing Sheet

BACKGROUND OF THE VARIETY

Field of the Invention

In the field of plant genetics we conduct an extensive and continuing plant-breeding program including the origination and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

Prior Varieties

Among the existent varieties of plum and interspecific trees, which are, known to us, and mentioned herein, are 'Autumn Giant' Plum (U.S. Plant Pat. No. 5,624), 'Red Beaut' Plum (U.S. Plant Pat. No. 2,539) and 'Flavorich' Interspecific (U.S. Plant Pat. No. 8,546).

ORIGIN OF THE VARIETY

The present new and distinct variety of interspecific tree [*Prunus salicina*×(*Prunus salician*×(*Prunus salicina*× *Prunus armeniaca*))] was developed by us in our experimental orchard located near Modesto, Calif., as a first generation cross between two seedlings with field identification numbers 73ED135 and 72GC211. There selections were previously selected by us to be used as future parents in our on going stone fruit breeding program. The maternal parent (43ED135) originated from a cross between a plum seedling of unknown parentage with 'Autumn Giant' Plum (U.S. Plant Pat. No. 5,624). The paternal parent (72GC211) originated from a cross between a plum seedling of unknown parentage with the plumcot 46G865. The plumcot 46G865 originated from a cross of 'Red Beaut' Plum (U.S. Plant Pat. No. 2,539) with an apricot of unknown parentage.

We planted and maintained a large group of these first generation crosses growing on their own root system. Under close observation we recognized the desirable fruit characteristics of the present variety and selected it in 1994 for asexual propagation and commercialization.

ASEXUAL REPRODUCTION OF THE VARIETY

Asexual reproduction of the distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The herein distinct variety of interspecific tree (plum×(plum×plumcot)) is of medium size, vigorous, yellow flesh, semi-freestone fruit with very good flavor and eating quality. The fruit is further characterized by having firm flesh, good storage and shipping quality, being relatively uniform in size throughout the tree and holding firm on the tree from 10 to 14 days after maturity. In comparison to the fruit of the late maturing Plum 'Autumn Giant' (U.S. Plant Pat. No. 5,624), the new variety is blackish blue in color compared to red, is approximately equal in size, and is approximately 2 weeks earlier in maturity. In comparison to the fruit of the Interspecific tree 'Flavorich' (U.S. Plant Pat. No. 8,546), the fruit of the new variety is more round in shape, and is approximately 10 days earlier in maturity.

PHOTOGRAPH OF THE VARIETY

The accompanying color photographic illustration shows typical specimens of the foliage and fruit of the present interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the present variety of interspecific tree, its flowers, foliage and fruit, as based on observations of 6 year old specimens on 'Nemaguard' Rootstock (non-patented), growing near Modesto, Calif., with color terminology (except those in common terms) in accordance with Reinhold Color Atlas by A. Kornerup and J. H. Wanscher.

Tree:

*Size*.—Medium. Tree reduced by pruning to 10 to 12 feet in height primarily for economical harvesting of fruit.

*Vigor*.—Vigorous. Growth of 5 to 6 feet the first growing season, varies slightly with soil fertility and climatic conditions.

*Form*.—Upright. Tree growth is upright in early growth period; the width increases with heavy production of fruit.

*Branching habit*.—Upright with crotch angle approximately 30 to 35 degrees.

*Productivity*.—Productive. Fruit set 1½ or more times desired for normal crop load and thinning is necessary.

*Density*.—Medium dense. Usually pruned to vase shape to allow more sunlight to center of tree to enhance fruit color and growth of fruitwood.

*Bearer*.—Regular. Adequate fruit set 5 consecutive years. No alternate bearing observed.

*Fertility*.—Self-sterile, needs pollenizer. Some of the factors affecting blooming date that must be considered when selecting pollenizer for specific areas. Winter chilling hours, number of heat units to excite bud initiation, type of rootstocks, soil type, cultural practices and climatic conditions.

*Hardiness*.—Tree grown in USDA Hardiness Zone 9. Winter chilling requirement is approximately 800 to 900 hours at 45° F. or below. Hardy in all stone fruit growing areas of California.

Trunk:

*Size*.—Medium stocky. Average circumference 18 inches at 14 inches above ground level on a six year old tree.

*Texture*.—Medium shaggy. Shagginess increases with age of growth.

*Color*.—Brown to tobacco brown (5-E-3) to (5-E-6).

Branches:

*Size*.—Medium. Average circumference of 6½ inches at 34 inches above ground. Crotch angle approximately 30 to 35°.

*Texture*.—Smooth on first years growth, medium rough as branches become larger and older.

*Lenticels*.—Numerous. Approximately 48 per 4 square inch surface. Color — mustard brown to oak brown (5-E-6) to (5-D-6). Size — Average length 3/32 inch. Average width 1/32 inch. Size increases with growth of branch.

*Color*.—One year old wood light green to light tan (3-D-7) to (4-C-6). Older mature branches vary from light brown to beaver brown (5-D-5) to (5-E-4). Color varies with age of growth.

Leaves:

*Size*.—Large. Average length — 4 23/32 inches. Average width — 1 13/32 inches.

*Form*.—Obovate.

*Apex*.—Acuminate.

*Base*.—Cuneate.

*Margin*.—Doubly serrate.

*Thickness*.—Medium.

*Surface*.—Upper surface relatively smooth, slightly indented over leaf veins, glabrous. Lower surface — relatively smooth, small ridges created by midrib and pinnate venation, glabrous.

*Petiole*.—Average length — 5/8 inch. Average width — 5/64 inch. Color — pale green to light green (30-A-3) to (30-A-4).

*Glands*.—Size — small, round. Average diameter 1/32 inch. Globose. Number varies from 1 to 4. Average number 3. Color — varies from grayish green in center to reddish brown on outer edges (1-C-6) to (9-D-5), becomes darker with age. Located on the upper portion of the petiole and the base of the leaf blade.

*Color*.—Upper surface green to dark green (30-E-5) to (30-E-6). Lower surface grayish green to green (30-D-4) to (30-D-6).

Flower buds:

*Size*.—Small. Average length — 11/32 inch. Average diameter — 3/16 inch.

*Hardiness*.—Hardy with respect to California winters, grown in USDA Hardiness Zone 9.

*Form* .—Plump, free, conical, elongated as bud matures.

*Spur*.—Number of buds per spur varies from 2 to 10. Average number 6, varies with age of spur.

*Pedicel*.—Average length 15/64 inch. Average width 3/64 inch. Color — pale green to light green (29-A-2) to (29-A-3).

*Color*.—White (30-A-1).

*Pubescence*.—Wanting.

Flowers:

*Size*.—Medium. Average height — 25/64 inch. Average diameter — 49/64 inch.

*Petals*.—Number — five, alternately arranged with sepals. Average length 11/32 inch. Average width 17/64 inch. Shape — obovate, narrows at point of attachment. Surface — Relatively smooth, slightly undulated, apex and sides curved and cupped to create bowl shape around anthers and pistil. Outer edges vary from smooth to scalloped. Color — white (30-A-1).

*Sepals*.—Number — five, alternately positioned to petals. Average length 9/64 inch. Average width 7/64 inch. Color — lower surface; grayish green (28-C-6. Upper surface yellowish green (28-B-6). Both surfaces glabrous.

*Stamens*.—Numbers range from 38 to 42 per flower. Average number 40. Filament color — white (30-A-1). Average length — 13/64 inch. Anther color — golden yellow to brownish yellow (5-B-8) to (5-C-8).

*Pollen*.—Abundant, pollen sac full. Self-sterile, pollenizer required. Some of the factors affecting blooming date that must be considered when selecting pollenizer for specific areas. Winter chilling hours, number of heat units to excite bud initiation, type of rootstock, soil type, cultural practices and climatic conditions. Color varies from light yellow to butter yellow (3-A-5) to (4-A-5).

*Pistil.*—Normally 1, varies from 1 to 2. Average length — 3/8 inch. Color — yellowish white to pale yellow (3-A-2) to (3-A-3). Stigma approximately 3/32 inch above anthers.

*Fragrance.*—Very slight.

*Blooming period.*—Date of first bloom: Mar. 4, 2000. Date of petal fall: Mar. 12, 2000. Varies slightly with climatic conditions.

*Color.*—White (30-A-1).

*Pedicel.*—Average length — 15/64 inch. Average width 3/64 inch. Color — pale green to yellowish green (30-A-5) to (30-B-5).

*Flowers per bud.*—Average number 2. Varies from 1 to 3.

Fruit:

*Maturity when described.*—Firm ripe.

*Date of first picking.*—Sep. 4, 2000.

*Date of last picking.*—Sep. 9, 2000. Varies slightly with climatic conditions.

*Size.*—Large. Average diameter axially 2 5/32 to 2 3/8 inches. Average transversely in suture plane 2 1/2 to 2 21/32 inches. Average weight 144.8 grams. Average weight varies slightly with fertility of the soil, amount of thinning and climatic conditions.

*Form.*—Globose. Fruit relatively uniform, slightly flattened at apex and base.

*Suture.*—Shallow, extends from base to apex.

*Ventral surface.*—Smooth, nearly rounded.

*Apex.*—Varies from flat to slightly retuse.

*Base.*—Retuse.

*Cavity.*—Rounded, slightly elongated in suture plane. Average depth — 5/16 inch. Average breadth — 15/32 inch.

Flesh:

*Ripens.*—Uniform, evenly.

*Texture.*—Firm, meaty.

*Fibers.*—Few, small, tender.

*Firmness.*—Good, similar to 'Flavorich'.

*Aroma.*—Very slight.

*Amydgalin.*—None.

*Eating quality.*—Very good.

*Flavor.*—Very good. Good balance between sugar and acid.

*Juice.*—Moderate, enhances flavor.

*Brix.*—19.9°, varies slightly with number of fruit per tree and climatic conditions.

*Color.*—Yellow white to plae yellow (4-A-2) to (4-A-3), varies slightly with fruit maturity. Pit cavity brownish yellow to Indian yellow (5-B-7) to (5-E-8).

Stem:

*Size.*—Average length — 3/8 inch. Average width — 1/8 inch. Enlarged at fruit attachment.

*Color.*—Light brown to brown (6-D-6) to (6-E-5).

Skin:

*Thickness.*—Medium thickness, shows minimal scarring or tearing during picking and packing trials.

*Surface texture.*—Relatively smooth, slightly waffled.

*Bloom.*—Moderate, covers entire surface.

*Tendency to crack.*—Slight.

*Color.*—Uniform, complete coverage. Dark violet to blackish blue (18-F-2) to (18-F-3).

*Tanacity.*—Tenacious to flesh.

*Astringency.*—None.

*Pubescence.*—Wanting.

Stones:

*Type.*—Semi-freestone, slight flesh attachment along suture.

*Size.*—Small. Average length — 3/4 inch. Average width — 5/8 inch. Average thickness — 3/8 inch.

*Form.*—Obovoid.

*Base.*—Varies from rounded to nearly flat.

*Apex.*—Cuspidate. Length — Short, 3/64 inch.

*Surface.*—Very lightly pitted throughout, three to four small ridges starting at base and extending toward apex approximately 1/3 the length of the stone. One long, narrow ridge on each side of suture.

*Sides.*—Equal to unequal. Some stones extend outward further on one side from suture plane.

*Tendency to split.*—None.

*Color.*—Light brown to tile red (7-D-5) to (7-D-7) when dry.

Use: Dessert. Market — local and long distance.

Keeping quality: Good, held firm in cold storage 2 weeks at 38 to 42° F. without internal breakdown or appreciable loss of flavor.

Shipping quality: Good, minimal bruising of flesh or skin scarring in picking and packing trials.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, being a regular and productive bearer of large, semi-freestone fruit with very good flavor and eating quality and, in comparison to the Interspecific tree 'Flavorich' (U.S. Plant Pat. No. 8,546) the fruit of the new variety is more rounded in shape, has a slightly waffled skin surface compared to smooth, and is approximately 10 to 12 days earlier in maturity.

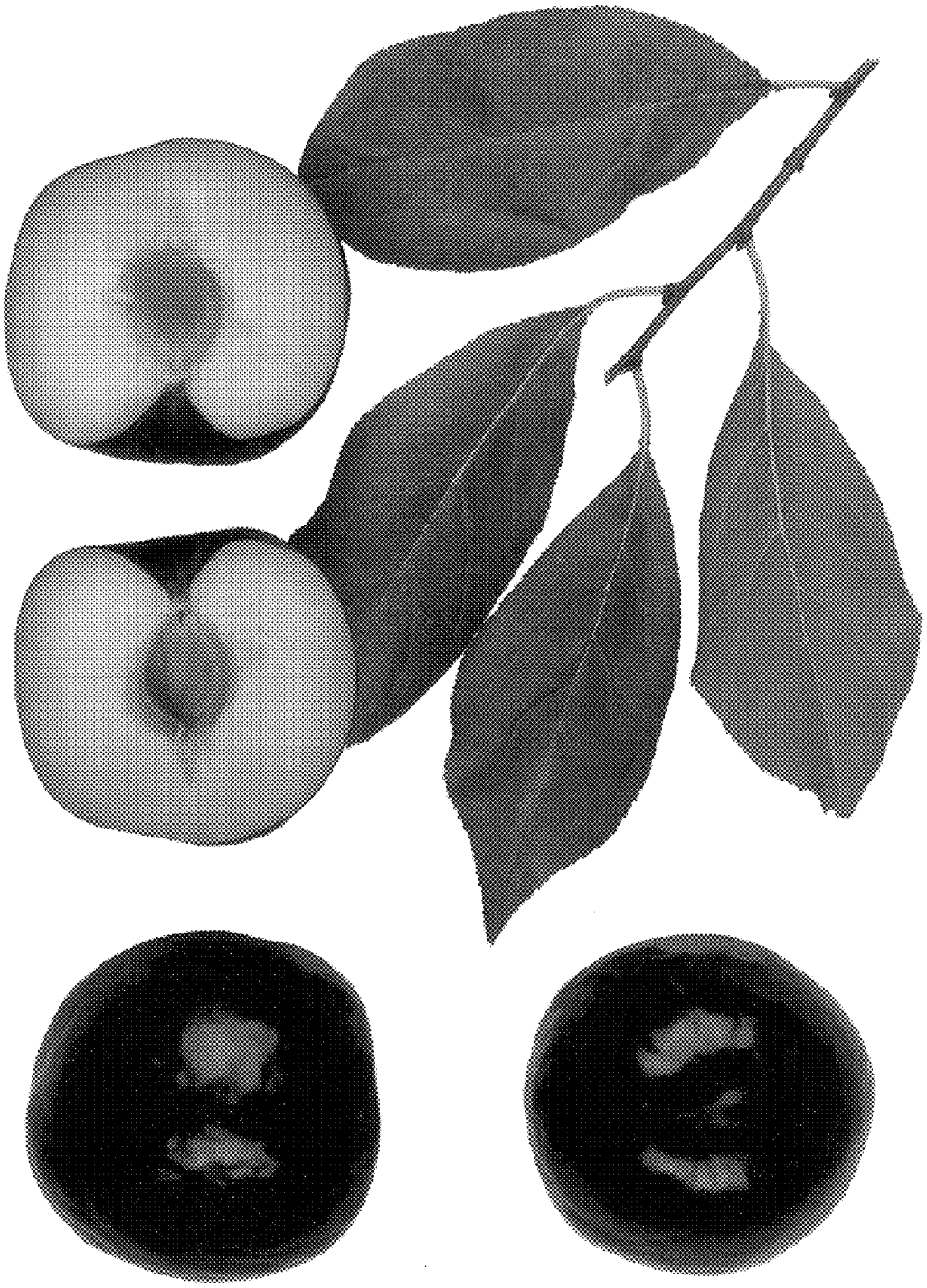

* * * * *